US009000268B2

(12) United States Patent
Skrsyniarz

(10) Patent No.: US 9,000,268 B2
(45) Date of Patent: Apr. 7, 2015

(54) TAMARINDO LETTUCE VARIETY

(75) Inventor: Monia Skrsyniarz, Brézé (FR)

(73) Assignee: Enza Zaden Beheer B.V., Enkhuizen (NL)

(*) Notice: Subject to any disclaimer, the term of this patent is extended or adjusted under 35 U.S.C. 154(b) by 290 days.

(21) Appl. No.: 13/561,728

(22) Filed: Jul. 30, 2012

(65) Prior Publication Data

US 2014/0033339 A1    Jan. 30, 2014

(51) Int. Cl.
*A01H 5/12*    (2006.01)

(52) U.S. Cl.
CPC .......................................... *A01H 5/12* (2013.01)

(58) Field of Classification Search
None
See application file for complete search history.

(56) References Cited

U.S. PATENT DOCUMENTS

| | | |
|---|---|---|
| 5,304,719 A | 4/1994 | Segebart |
| 5,367,109 A | 11/1994 | Segebart |
| 5,523,520 A | 6/1996 | Hunsperger et al. |
| 5,763,755 A | 6/1998 | Carlone |
| 5,850,009 A | 12/1998 | Kevern |
| 5,973,232 A | 10/1999 | Waycott et al. |
| 6,492,579 B2 | 12/2002 | Olivas et al. |
| 6,903,249 B2 | 6/2005 | Lambalk et al. |
| 7,115,799 B2 | 10/2006 | De Jong |
| 7,371,934 B1 | 5/2008 | Skrsyniarz |
| 7,427,699 B1 | 9/2008 | Skrsyniarz |
| 7,501,555 B2 | 3/2009 | Lambalk et al. |
| 7,534,941 B1 | 5/2009 | Avila et al. |
| 7,705,206 B2 | 4/2010 | Waycott |
| 7,790,948 B2 | 9/2010 | Lambalk et al. |
| 7,977,536 B2 | 7/2011 | Holland et al. |
| 8,183,437 B2 | 5/2012 | Waycott |
| 8,188,340 B2 | 5/2012 | Holland et al. |
| 8,203,034 B2 | 6/2012 | Waycott |
| 8,212,114 B2 | 7/2012 | Holland et al. |
| 8,212,115 B2 | 7/2012 | Holland et al. |
| 8,212,116 B2 | 7/2012 | Lemont et al. |
| 8,404,936 B2* | 3/2013 | Skrsyniarz ..................... 800/305 |
| 2010/0299777 A1 | 11/2010 | Lambalk et al. |
| 2011/0197295 A1 | 8/2011 | Schryve |
| 2011/0277176 A1 | 11/2011 | Conijn |
| 2011/0296549 A1 | 12/2011 | Holland |
| 2012/0005771 A1 | 1/2012 | Nannes |
| 2012/0005772 A1 | 1/2012 | Nannes |
| 2012/0011611 A1 | 1/2012 | Holland |
| 2012/0011612 A1 | 1/2012 | Skrsyniarz |
| 2012/0011613 A1 | 1/2012 | Skrsyniarz |
| 2012/0042405 A1 | 2/2012 | Lemont |
| 2012/0042406 A1 | 2/2012 | Lemont |
| 2012/0073011 A1 | 3/2012 | Conijn et al. |
| 2012/0222149 A1 | 8/2012 | Nannes |
| 2013/0024984 A1 | 1/2013 | Skrsyniarz |
| 2013/0031663 A1 | 1/2013 | Sinclair et al. |
| 2013/0081149 A1 | 3/2013 | Lemont |

FOREIGN PATENT DOCUMENTS

WO    2000/063432 A1    10/2000

OTHER PUBLICATIONS

Bassett, M. J., "The Role of Leaf Shape in the Inheritance of Heading in Lettuce (*Lactuca sativa* L.)", Journal of the American Society for Horticultural Science, vol. 100, No. 2, 1975, pp. 104-105.
Bennetzen et al., "Approaches and Progress in the Molecular Cloning of Plant Disease Resistance Genes", Genetic Engineering, vol. 14, Edited by J.K. Setlow, Plenum Press, New York, 1992, pp. 99-124.
Bonnier et al., "New Sources of Major Gene Resistance in Lactuca to *Bremia Lactucae*", Euphytica, vol. 61, 1992, pp. 203-211.
De Bolle et al., "Antimicrobial Peptides from *Mirabilis Jalapa* and *Amaranthus Caudatus*: Expression, Processing, Localization and Biological Activity in Transgenic Tobacco", Plant Molecular Biology, vol. 31, 1996, pp. 993-1008.
De Vries et al., "Numerical Morphological Analysis of Lettuce Cultivars and Species (*Lactuca* Sect. *Lactuca*, Asteraceae)", Plant Systematics and Evolution, vol. 193, 1994, pp. 125-141.
Dufresne et al., "Genetic Sequences: How are they Patented?", Nature Biotechnology, vol. 22, No. 2, Feb. 2004, pp. 231-232.
Eshed et al., "Less-Than-Additive Epistatic Interactions of Quantitative Trait Loci in Tomato", Genetics Society of America, vol. 143, Aug. 1996, pp. 1807-1817.
Farrara et al., "Genetic Analysis of Factors for Resistance to Downy Mildew (*Bremia lactucae*) in Species of Lettuce (*Lactuca sativa* and *L. serriola*)", Plant Pathology, vol. 36, 1987, pp. 499-514.
Farrara et al., "Identification of New Sources of Resistance to Downy Mildew in *Lactuca* Spp.", HortScience, vol. 22, No. 4, Aug. 1987, pp. 647-649.
Holland, Melvin Oris, Unpublished U.S. Appl. No. 13/449,193, filed on Apr. 17, 2012, titled "Cuervo Lettuce Variety", 36 pages.
Kessell et al., "Recessive Resistance to *Plasmopara lactucae-radicis* Maps by Bulked Segregant Analysis to a Cluster of Dominant Disease Resistance Genes in Lettuce", Molecular Plant-Microbe Interactions, vol. 6. No. 6, 1993, pp. 722-728.
Kraft et al., "Linkage Disequilibrium and Fingerprinting in Sugar Beet", Theor. Appl. Genet., vol. 101, 2000, pp. 323-326.
Landry et al., "A Genetic Map of Lettuce (*Lactuca sativa* L.) with Restriction Fragment Length Polymorphism, Isozyme, Disease Resistance and Morphological Markers", Genetics Society of America, vol. 116, Jun. 1987, pp. 331-337.
Lebeda et al., "Further Investigation of the Specificity of Interactions between Wild *Lactuca* Spp. and *Bremia lactucae* Isolates from *Lactuca serriola*", Journal of Phytopathology, vol. 133, 1991, pp. 57-64.
Lemont, Magali, Unpublished U.S. Appl. No. 13/462,754, filed on May 2, 2012, titled "Ocate Lettuce Variety", 36 pages.
Lemont, Magali, Unpublished U.S. Appl. No. 13/470,774, filed on May 14, 2012, titled "Chicoma Lettuce Variety", 36 pages.
Lemont, Magali, Unpublished U.S. Appl. No. 13/471,165, filed on May 14, 2012, titled "Capulin Lettuce Variety", 36 pages.

(Continued)

*Primary Examiner* — Eileen B O Hara
(74) *Attorney, Agent, or Firm* — Morrison & Foerster LLP

(57) ABSTRACT

A new lettuce variety designated 'Tamarindo' is described. 'Tamarindo' is a cutting lettuce variety exhibiting stability and uniformity.

13 Claims, No Drawings

(56) References Cited

OTHER PUBLICATIONS

Maisonneuve et al., "Rapid Mapping of Two Genes for Resistance to Downy Mildew from *Lactuca serriola* to Existing Clusters of Resistance Genes", Theor. Appl. Genet. vol. 89, 1994, pp. 96-104.

Maisonneuve et al., "Sexual and Somatic Hybridization in the Genus *Lactuca*", Euphytica, vol. 85, 1995, pp. 281-285.

Maisonneuve et al., "Inheritance of Resistance to Beet Western Yellows Virus in *Lactuca virosa* L.", HortScience, vol. 26, No. 12, Dec. 1991, pp. 1543-1545.

Maisonneuve, Brigitte, "*Lactuca virosa*, A Source of Disease Resistance Genes for Lettuce Breeding: Results and Difficulties for Gene Introgression", Eucarpia Leafy Vegetables, 2003, pp. 61-67.

Maisonneuve, Brigitte, "Utilisation de la Culture in vitro d'embryons Immatures Pour Les Croisements Interspecifiques Entre *Lactuca sativa* L. et *L. saligna* L. ou *L. virosa* L. ; Etude Des Hybrides Obtenus", ("Interspecific Hybridization in *Lactuca* sp. using in Vitro Culture of Immature Embryos, and Study of Hybrid Offspring)", Agronomie, vol. 7, No. 5, 1987, pp. 313-319 (English Abstract Submitted).

Michelmore et al., "Clusters of Resistance Genes in Plants Evolve by Divergent Selection and a Birth-and-Death Process", Genome Research, vol. 8, 1998, pp. 1113-1130.

Michelmore et al., "The Inheritance of Virulence in *Bremia lactucae* to Match Resistance Factors 3, 4,5,6,8,9,10 and 11 in lettuce (*Lactuca sativa*)", Plant Pathology, vol. 33, 1984, pp. 301-315.

Michelmore et al., "Molecular Markers and Genome Analysis in the Manipulation of Lettuce Downy Mildew", Advances in Molecular Genetics of Plant-Microbe Interactions, 1993, pp. 517-523.

Michelmore et al., "Transformation of Lettuce (*Lactuca sativa*) Mediated by *Agrobacterium tumefaciens*", Plant Cell Reports, vol. 6, 1987, pp. 439-442.

Nannes, Johannes Simon Petrus, Unpublished U.S. Appl. No. 13/478,858, filed on May 23, 2012, titled "Holon Lettuce Variety", 34 pages.

Nannes, Johannes Simon Petrus, Unpublished U.S. Appl. No. 13/524,996, filed on Jun. 15, 2012, titled "Ansar Lettuce Variety", 34 pages.

Nannes, Johannes Simon Petrus, Unpublished U.S. Appl. No. 13/525,044, filed on Jun. 15, 2012, titled "Venado Lettuce Variety", 34 pages.

Nannes, Johannes Simon Petrus, Unpublished U.S. Appl. No. 13/525,074, filed on Jun. 15, 2012, titled "Poloma Lettuce Variety", 34 pages.

Nannes, Johannes Simon Petrus, Unpublished U.S. Appl. No. 13/563,384, filed on Jul. 31, 2012, titled "Truchas Lettuce Variety", 34 pages.

Pang et al., "Expression of a Gene Encoding a Scorpion Insectotoxin Peptide in Yeast, Bacteria and Plants", Gene, vol. 116, 1992, pp. 165-172.

Paran et al., "Development of Reliable PCR-based Markers Linked to Downy Mildew Resistance Genes in Lettuce", Theory of Applied Genetics, vol. 85, 1993, pp. 985-993.

Paran et al., "Identification of Restriction Fragment Length Polymorphism and Random Amplified Polymorphic DNA Markers Linked to Downy Mildew Resistance Genes in Lettuce, Using Near-Isogenic Lines", Genome, vol. 34, 1991, pp. 1021-1027.

Ryder et al., "Inheritance and Epistasis Studies of Chlorophyll Deficiency in Lettuce", J. Amer. Soc. Hort. Sci., vol. 124, No. 6, 1999, pp. 636-640.

Ryder, Edward J., "Lettuce Genetics: Inheritance, Linkage and Epistasis", J. Amer. Soc. Hort. Sci., vol. 117, No. 3, 1992, pp. 504-507.

Skrsyniarz, Monia, Unpublished U.S. Appl. No. 13/462,622, filed on May 2, 2012, titled "Pommegranate Crunch Lettuce Variety", 36 pages.

Skrsyniarz, Monia, Unpublished U.S. Appl. No. 13/526,131, filed on Jun. 18, 2012, titled "Poneloya Lettuce Variety", 34 pages.

Stam, Piet, "Construction of Integrated Genetic Linkage Maps by Means of a New Computer Package: JoinMap", The Plant Journal, vol. 3, No. 5, 1993, pp. 739-744.

Thomas et al., "Lettuce Production in the United States", In Agriculture Handbook No. 221. Agricultural Research Service of the United States Department of Agriculture, Revised Aug. 1974, 3 pages.

Vriend, Ronald Jan, Unpublished U.S. Appl. No. 13/564,462, filed on Aug. 1, 2012, titled "Mead Lettuce Variety", 34 pages.

Waycott et al., "Differentiation of Nearly Identical Germplasm Accessions by a Combination of Molecular and Morphologic Analyses", Genome, vol. 37, No. 4, 1994, pp. 577-583.

Williams et al., "DNA Polymorphisms Amplified by Arbitrary Primers are useful as Genetic Markers", Nucleic Acids Research, vol. 18, No. 22, 1990, pp. 6531-6535.

Winsemius, Geertje, Unpublished U.S. Appl. No. 13/493,294, filed on Jun. 11, 2012, titled Mirlo Lettuce Variety, 36 pages.

Xinrun et al., "Genotypic Effects on Tissue Culture Response of Lettuce Cotyledons", J. Genet. & Breed., vol. 46, 1992, pp. 287-290.

Non Final Office Action received for U. S. Appl. No. 09/959,037, mailed on Aug. 13, 2003, 10 pages.

Final Office Action received for U.S. Appl. No. 09/959,037, mailed on Oct. 6, 2004, 9 pages.

Non Final Office Action received for U.S. Appl. No. 12/887,213, mailed on Oct. 12, 2012, 11 pages.

Non Final Office Action received for U.S. Appl. No. 13/034,349, mailed on Dec. 6, 2012, 11 pages.

Notice of Allowance received for U.S. Appl. No. 13/034,349, mailed on Apr. 30, 2013, 6 pages.

Notice of Allowance received for U.S. Appl. No. 09/959,037, mailed on Oct. 26, 2004, 10 pages.

Non Final Office Action received for U.S. Appl. No. 10/652,731, mailed on Oct. 22, 2004, 22 pages.

Notice of Allowance received for U.S. Appl. No. 10/652,731, mailed on Apr. 1, 2005, 8 pages.

Non Final Office Action received for U.S. Appl. No. 11/146,392, mailed on Nov. 14, 2007, 13 pages.

Final Office Action received for U.S. Appl. No. 11/146,392, mailed on Aug. 13, 2008, 10 pages.

Notice of Allowance received for U.S. Appl. No. 11/146,392, mailed on Oct. 30, 2008, 7 pages.

Non Final Office Action received for U.S. Appl. No. 11/671,251, mailed on Aug. 23, 2007, 9 pages.

Notice of Allowance received for U.S. Appl. No. 11/671,251, mailed on Jan. 29, 2008, 6 pages.

Non Final Office Action received for U.S. Appl. No. 11/746,785, mailed on Nov. 30, 2007, 9 pages.

Notice of Allowance received for U.S. Appl. No. 11/746,785, mailed on May 19, 2008, 5 pages.

Non Final Office Action received for U.S. Appl. No. 12/241,351, mailed on Oct. 20, 2010, 9 pages.

Notice of Allowance received for U.S. Appl. No. 12/241,351, mailed on Mar. 4, 2011, 5 pages.

Notice of Allowance received for U.S. Appl. No. 12/362,556, mailed on Apr. 13, 2010, 7 pages.

Non Final Office Action received for U.S. Appl. No. 12/569,751, mailed on Sep. 12, 2011, 10 pages.

Notice of Allowance received for U.S. Appl. No. 12/569,751, mailed on Feb. 2, 2012, 8 pages.

Non Final Office Action received for U.S. Appl. No. 12/569,812, mailed on Sep. 9, 2011, 10 pages.

Notice of Allowance received for U.S. Appl. No. 12/569,812, mailed on Feb. 8, 2012, 8 pages.

Non Final Office Action received for U.S. Appl. No. 12/574,609, mailed on Sep. 12, 2011, 9 pages.

Notice of Allowance received for U.S. Appl. No. 12/574,609, mailed on Feb. 17, 2012, 5 pages.

Non Final Office Action received for U.S. Appl. No. 12/651,568, mailed on Sep. 12, 2011, 9 pages.

Notice of Allowance received for U.S. Appl. No. 12/651,568, mailed on Feb. 23, 2012, 5 pages.

Non Final Office Action received for U.S. Appl. No. 12/775,805, mailed on Mar. 28, 2012, 10 pages.

(56) References Cited

OTHER PUBLICATIONS

Notice of Allowance received for U.S. Appl. No. 12/775,805, mailed on Jan. 14, 2013, 5 pages.
Non Final Office Action received for U.S. Appl. No. 12/788,869 mailed on Jun. 15, 2012, 10 pages.
Notice of Allowance received for U.S. Appl. No. 12/788,869, mailed on Apr. 3, 2013, 6 pages.
Non Final Office Action received for U.S. Appl. No. 12/828,842 mailed on Jun. 21, 2012, 10 pages.
Notice of Allowance received for U.S. Appl. No. 12/828,842 mailed on Apr. 2, 2013, 6 pages.
Non Final Office Action received for U.S. Appl. No. 12/829,053 mailed on Jun. 22, 2012, 10 pages.
Notice of Allowance received for U.S. Appl. No. 12/829,053, mailed on Apr. 24, 2013, 6 pages.
Non Final Office Action received for U.S. Appl. No. 12/830,753 mailed on Jun. 22, 2012, 11 pages.
Notice of Allowance received for U.S. Appl. No. 12/830,753, mailed on Dec. 14, 2012, 5 pages.
Non Final Office Action Received for U.S. Appl. No. 12/832,387, mailed on Jul. 13, 2012, 10 pages.
Notice of Allowance received for U.S. Appl. No. 12/832,387, mailed on May 2, 2013, 6 pages.
Non Final Office Action Received for U.S. Appl. No. 12/832,405, mailed on Jun. 28, 2012, 10 pages.
Notice of Allowance received for U.S. Appl. No. 12/832,405, mailed on Dec. 13, 2012, 5 pages.
Non Final Office Action received for U.S. Appl. No. 12/853,881, mailed on Dec. 10, 2010, 11 pages.
Final Office Action received for U.S. Appl. No. 12/853,881, mailed on Aug. 9, 2011, 12 pages.
Non Final Office Action received for U.S. Appl. No. 12/857,275, mailed on Jul. 26, 2012, 10 pages.
Notice of Allowance received for U.S. Appl. No. 12/857,275, mailed on Apr. 24, 2013, 6 pages.
Non Final Office Action Received for U.S. Appl. No. 12/857,346, mailed on Jul. 13, 2012, 10 pages.
Notice of Allowance received for U.S. Appl. No. 12/857,346, mailed on Apr. 24, 2013, 6 pages.
Holland, Melvin Oris, Unpublished U.S. Appl. No. 13/828,918, filed on Mar. 14, 2013, titled "Lettuce Variety 'Arroyo'", 37 pages.
Lemont, Magali, Unpublished U.S. Appl. No. 13/792,681, filed on Mar. 11, 2013, titled "Lettuce Variety E01L1935", 36 pages.
Lemont, Magali, Unpublished U.S. Appl. No. 13/792,771, filed on Mar. 11, 2013, titled "Lettuce Variety E01L1937", 36 pages.
Lemont, Magali, Unpublished U.S. Appl. No. 13/797,130, filed on Mar. 12, 2013, titled "Lettuce Variety 'E01L30144", 36 pages.
Sinclair, Jonathan Walker, Unpublished U.S. Appl. No. 13/587,496, filed on Aug. 16, 2012, titled "Bandelier Lettuce Variety", 36 pages.
Holland, Melvin O., Unpublished U.S. Appl. No. 13/938,960, filed on Jul. 10, 2013, titled "Pennylea Lettuce Variety", 35 pages.
Non Final Office Action received for U.S. Appl. No. 13/193,389, mailed on Aug. 19, 2013, 10 pages.
Non Final Office Action received for U.S. Appl. No. 13/189,264, mailed on Aug. 8, 2013, 10 pages.

* cited by examiner

TAMARINDO LETTUCE VARIETY

FIELD OF THE INVENTION

The present invention relates to the field of plant breeding. In particular, this invention relates to a new lettuce, *Lactuca sativa* variety designated 'Tamarindo'.

BACKGROUND OF THE INVENTION

Cultivated forms of lettuce belong to the highly polymorphic species *Lactuca sativa* that is grown for its edible head and leaves. As a crop, lettuce is grown commercially wherever environmental conditions permit the production of an economically viable yield. For planting purposes, the lettuce season is typically divided into three categories (i.e., early, mid, and late), with coastal areas planting from January to August, and desert regions planting from August to December. Fresh lettuce is consumed nearly exclusively as fresh, raw product and occasionally as a cooked vegetable.

*Lactuca sativa* is in the Cichorieae tribe of the Asteraceae (Compositae) family. Lettuce is related to chicory, sunflower, aster, dandelion, artichoke, and chrysanthemum. Sativa is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce, also known as cutting lettuce, comes in many varieties, none of which form a head, and include the green oak leaf variety. Latin lettuce looks like a cross between romaine and butterhead. Stem lettuce has long, narrow leaves and thick, edible stems. Oilseed lettuce is a type grown for its large seeds that are pressed to obtain oil.

Lettuce is an increasingly popular crop. Worldwide lettuce consumption continues to increase. As a result of this demand, there is a continued need for new lettuce varieties. In particular, there is a need for improved cutting lettuce varieties that are stable, high yielding, and agronomically sound.

SUMMARY OF THE INVENTION

In order to meet these needs, the present invention is directed to improved lettuce varieties. In one embodiment, the present invention is directed to lettuce, *Lactuca sativa*, seed designated as 'Tamarindo' having ATCC Accession Number PTA-13146. In one embodiment, the present invention is directed to a *Lactuca sativa* lettuce plant and parts isolated therefrom produced by growing 'Tamarindo' lettuce seed. In another embodiment, the present invention is directed to a *Lactuca sativa* plant and parts isolated therefrom having all the physiological and morphological characteristics of a *Lactuca sativa* plant produced by growing 'Tamarindo' lettuce seed having ATCC Accession Number PTA-13146. In still another embodiment, the present invention is directed to an $F_1$ hybrid *Lactuca sativa* lettuce seed, plants grown from the seed, and a head isolated therefrom having 'Tamarindo' as a parent, where 'Tamarindo' is grown from 'Tamarindo' lettuce seed having ATCC Accession Number PTA-13146.

Lettuce plant parts include lettuce heads, lettuce leaves, parts of lettuce leaves, pollen, ovules, flowers, and the like. In another embodiment, the present invention is further directed to lettuce heads, lettuce leaves, parts of lettuce leaves, flowers, pollen, and ovules isolated from 'Tamarindo' lettuce plants. In another embodiment, the present invention is further directed to tissue culture of 'Tamarindo' lettuce plants, and to lettuce plants regenerated from the tissue culture, where the plant has all of the morphological and physiological characteristics of 'Tamarindo' lettuce plants.

In still another embodiment, the present invention is further directed to packaging material containing 'Tamarindo' plant parts. Such packaging material includes but is not limited to boxes, plastic bags, etc. The 'Tamarindo' plant parts may be combined with other plant parts of other plant varieties.

In yet another embodiment, the present invention is further directed to a method of selecting lettuce plants, by a) growing 'Tamarindo' lettuce plants where the 'Tamarindo' plants are grown from lettuce seed having ATCC Accession Number PTA-13146 and b) selecting a plant from step a). In another embodiment, the present invention is further directed to lettuce plants, plant parts and seeds produced by the lettuce plants where the lettuce plants are isolated by the selection method of the invention.

In another embodiment, the present invention is further directed to a method of breeding lettuce plants by crossing a lettuce plant with a plant grown from 'Tamarindo' lettuce seed having ATCC Accession Number PTA-13146. In still another embodiment, the present invention is further directed to lettuce plants, lettuce parts from the lettuce plants, and seeds produced therefrom where the lettuce plant is isolated by the breeding method of the invention. In some embodiments, the lettuce plant isolated by the breeding method is a transgenic lettuce plant.

In another embodiment, the present invention is directed to methods for producing a lettuce plant containing in its genetic material one or more transgenes and to the transgenic lettuce plant produced by those methods.

In another embodiment, the present invention is directed to methods for producing a male sterile lettuce plant by introducing a nucleic acid molecule that confers male sterility into a lettuce plant produced by growing 'Tamarindo' lettuce seed, and to male sterile lettuce plants produced by such methods.

In another embodiment, the present invention is directed to methods of producing an herbicide resistant lettuce plant by introducing a gene conferring herbicide resistance into a lettuce plant produced by growing 'Tamarindo' lettuce seed, where the gene is selected from glyphosate, sulfonylurea, imidazolinone, dicamba, glufosinate, phenoxy proprionic acid, L-phosphinothricin, cyclohexone, cyclohexanedione, triazine, and benzonitrile. Certain embodiments are also directed to herbicide resistant lettuce plants produced by such methods.

In another embodiment, the present invention is directed to methods of producing a pest or insect resistant lettuce plan by introducing a gene conferring pest or insect resistance into a lettuce plant produced by growing 'Tamarindo' lettuce seed, and to pest or insect resistant lettuce plants produced by such methods. In certain embodiments, the gene conferring pest or insect resistance encodes a *Bacillus thuringiensis* endotoxin.

In another embodiment, the present invention is directed to methods of producing a disease resistant lettuce plant by introducing a gene conferring disease resistance into a lettuce plant produced by growing 'Tamarindo' lettuce seed, and to disease resistant lettuce plants produced by such methods.

In another embodiment, the present invention is directed to methods of producing a lettuce plant with a value-added trait by introducing a gene conferring a value-added trait into a lettuce plant produced by growing 'Tamarindo' lettuce seed, where the gene encodes a protein selected from a ferritin, a nitrate reductase, and a monellin. Certain embodiments are also directed to lettuce plants having a value-added trait produced by such methods.

In another embodiment, the present invention is directed to methods of introducing a desired trait into lettuce variety 'Tamarindo', by: (a) crossing a 'Tamarindo' plant, where a sample of 'Tamarindo' lettuce seed was deposited under ATCC Accession Number PTA-13146, with a plant of another lettuce variety that contains a desired trait to produce progeny plants, where the desired trait is selected from male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'Tamarindo' plant to produce backcross progeny plants; (d) selecting for backcross progeny plants that have the desired trait and all of the physiological and morphological characteristics of lettuce variety 'Tamarindo'; and (e) repeating steps (c) and (d) two or more times in succession to produce selected third or higher backcross progeny plants that comprise the desired trait. Certain embodiments are also directed to lettuce plants produced by such methods, where the plants have the desired trait and all of the physiological and morphological characteristics of lettuce variety 'Tamarindo'. In certain embodiments, the desired trait is herbicide resistance and the resistance is conferred to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile. In other embodiments, the desired trait is insect or pest resistance and the insect or pest resistance is conferred by a transgene encoding a Bacillus thuringiensis endotoxin.

In another embodiment, the present invention provides for single gene converted plants of 'Tamarindo'. The single transferred gene may preferably be a dominant or recessive allele. Preferably, the single transferred gene will confer such traits as male sterility, herbicide resistance, insect or pest resistance, modified fatty acid metabolism, modified carbohydrate metabolism, resistance for bacterial, fungal, or viral disease, male fertility, enhanced nutritional quality, and industrial usage. The single gene may be a naturally occurring lettuce gene or a transgene introduced through genetic engineering techniques.

In a further embodiment, the present invention relates to methods for developing lettuce plants in a lettuce plant breeding program using plant breeding techniques including recurrent selection, backcrossing, pedigree breeding, restriction fragment length polymorphism enhanced selection, genetic marker enhanced selection, and transformation. Seeds, lettuce plants, and parts thereof, produced by such breeding methods are also part of the invention.

In addition to the exemplary aspects and embodiments described above, further aspects and embodiments will become apparent by reference by study of the following description.

DETAILED DESCRIPTION OF THE INVENTION

There are numerous steps in the development of novel, desirable lettuce germplasm. Plant breeding begins with the analysis of problems and weaknesses of current lettuce germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of lettuce plant breeding is to develop new, unique, and genetically superior lettuce varieties. A breeder can initially select and crosses two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial lettuce varieties thus requires the development of parental lettuce varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into lettuce varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); Fehr (1987); and "Carrots and Related Vegetable Umbelliferae," Rubatzky, V. E., et al. (1999).

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Big Vein virus. Big vein is a disease of lettuce caused by Lettuce Mirafiori Big Vein Virus which is transmitted by the fungus *Olpidium virulentus*, with vein clearing and leaf shrinkage resulting in plants of poor quality and reduced marketable value.

Bolting. The premature development of a flowering stalk, and subsequent seed, before a plant produces a food crop. Bolting is typically caused by late planting.

*Bremia lactucae*. An oomycete that causes downy mildew in lettuce in cooler growing regions.

Core length. Length of the internal lettuce stem measured from the base of the cut and trimmed head to the tip of the stem.

Corky root. A disease caused by the bacterium *Sphingomonas suberifaciens*, which causes the entire taproot to become brown, severely cracked, and non-functional.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

First water date. The date the seed first receives adequate moisture to germinate. This can and often does equal the planting date.

Gene. As used herein, "gene" refers to a segment of nucleic acid. A gene can be introduced into a genome of a species, whether from a different species or from the same species, using transformation or various breeding methods.

Head diameter. Diameter of the cut and trimmed head, sliced vertically, and measured at the widest point perpendicular to the stem.

Head height. Height of the cut and trimmed head, sliced vertically, and measured from the base of the cut stem to the cap leaf.

Head weight. Weight of saleable lettuce head, cut and trimmed to market specifications.

Lettuce Mosaic virus. A disease that can cause a stunted, deformed, or mottled pattern in young lettuce and yellow, twisted, and deformed leaves in older lettuce.

Maturity date. Maturity refers to the stage when the plants are of full size or optimum weight, in marketable form or shape to be of commercial or economic value.

*Nasonovia ribisnigri*. A lettuce aphid that colonizes the innermost leaves of the lettuce plant, contaminating areas that cannot be treated easily with insecticides.

Quantitative Trait Loci. Quantitative Trait Loci (QTL) refers to genetic loci that control to some degree, numerically representable traits that are usually continuously distributed.

Ratio of head height/diameter. Head height divided by the head diameter is an indication of the head shape; <1 is flattened, 1=round, and >1 is pointed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing or via genetic engineering where essentially all of the desired morphological and physiological characteristics of a line are recovered in addition to the single gene transferred into the line via the backcrossing technique or via genetic engineering.

Tip burn. Means a browning of the edges or tips of lettuce leaves that is a physiological response to a lack of calcium.

Wet date. The wet date corresponds to the first planting date of lettuce.

Overview of the Variety 'Tamarindo'

Lettuce variety 'Tamarindo' is a red baby leaf cutting lettuce variety. Additionally, lettuce variety 'Tamarindo' is resistant to *Bremia lactucae* (downy mildew) strains Bl:1, Bl:2, Bl:4-Bl:7, Bl:10, Bl:12-Bl:18, Bl:20-Bl:26; Bl:28; susceptible to lettuce mosaic virus (LMV) strain Ls-1; and susceptible to *Nasonovia ribisnigri* biotype Nr:0. Lettuce variety 'Tamarindo' is the result of numerous generations of plant selections chosen for its improved yield as compared to the 'Refugio' variety and its good red leaf color including on the backside of the leaf.

The variety has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in variety 'Tamarindo'.

Objective Description of the Variety 'Tamarindo'

Lettuce variety 'Tamarindo' has the following morphologic and other characteristics:

Plant type: Cutting
Seed:
Color: White
Mature Leaves:
Margin:
Hue of green color of outer leaves: Reddish
Intensity of color of outer leaves: Medium
Anthocyanin coloration: Present
Bolting:
Class: Medium
Disease/Pest Resistance:
Lettuce Mosaic Virus: Susceptible (common strain Ls-1)
Downy Mildew (*Bremia lactucae*): Resistant to Bl:1, Bl:2, Bl:4-Bl:7, Bl:10, Bl:12-Bl:18, and Bl:20-Bl:26; and Bl:28.
Pests:
*Nasonovia ribisnigri*: Susceptible to biotype 0

Comparisons to Commercial Lettuce Variety

Table 1 below compares some of the characteristics of cutting lettuce variety 'Tamarindo' with the commercial lettuce variety, 'Redza'. Column 1 lists the characteristics, column 2 shows the characteristics for lettuce variety 'Tamarindo', and column 3 shows the characteristics for lettuce variety 'Redza'.

TABLE 1

| Characteristic | 'Tamarindo' | 'Redza' |
| --- | --- | --- |
| Leaf thickness | Medium | Very thick |
| Resistance to *Bremia lactucae* strain Bl:22 | Resistant | Susceptible |

Further Embodiments

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector contains DNA that contains a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed lettuce plants using transformation methods as described below to incorporate transgenes into the genetic material of the lettuce plant(s).

Expression Vectors for Lettuce Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS*, 80:4803 (1983). Another commonly used selectable marker gene is the hygromycin phosphotransferase gene which confers resistance to the antibiotic hygromycin. Vanden Elzen, et al., *Plant Mol. Biol.*, 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.*, 86:1216 (1988); Jones, et al., *Mol. Gen. Genet.*, 210:86 (1987); Svab, et al., *Plant Mol. Biol.*, 14:197 (1990); Hille, et al., *Plant Mol. Biol.*, 7:171 (1986). Other selectable marker genes confer resistance to herbicides such as glyphosate, glufosinate, or bromoxynil. Comai, et al., *Nature*, 317:741-744 (1985); Gordon-Kamm, et al., *Plant Cell*, 2:603-618 (1990); and Stalker, et al., *Science*, 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.*, 13:67 (1987); Shah, et al., *Science*, 233:478 (1986); and Charest, et al., *Plant Cell Rep.*, 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., *Plant Mol. Biol.*, 5:387 (1987); Teeri, et al., *EMBO J.*, 8:343 (1989); Koncz, et al., *PNAS*, 84:131 (1987); and DeBlock, et al., *EMBO J.*, 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.*, 115:151a (1991). However, these in vivo methods for visualizing GUS activity have not proven useful for recovery of transformed cells because of low sensitivity, high fluorescent backgrounds, and limitations associated with the use of GUS genes as selectable markers.

More recently, a gene encoding Green Fluorescent Protein (GFP) has been utilized as a marker for gene expression in prokaryotic and eukaryotic cells. Chalfie, et al., *Science*, 263:802 (1994). GFP and mutants of GFP may be used as screenable markers.

Expression Vectors for Lettuce Transformation: Promoters

Genes included in expression vectors must be driven by a nucleotide sequence containing a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in lettuce. Optionally, the inducible promoter is operably linked to a nucleotide sequence encoding a signal sequence which is operably linked to a gene for expression in lettuce. With an inducible promoter, the rate of transcription increases in response to an inducing agent.

Any inducible promoter can be used in the instant invention. See Ward, et al., *Plant Mol. Biol.*, 22:361-366 (1993). Exemplary inducible promoters include, but are not limited to, that from the ACEI system which responds to copper (Meft, et al., *PNAS*, 90:4567-4571 (1993)); In2 gene from maize which responds to benzenesulfonamide herbicide safeners (Hershey, et al., *Mol. Gen. Genet.*, 227:229-237 (1991) and Gatz, et al., *Mol. Gen. Genet.*, 243:32-38 (1994)) or Tet repressor from Tn10 (Gatz, et al., *Mol. Gen. Genet.*, 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS*, 88:0421 (1991).

B. Constitutive Promoters:

A constitutive promoter is operably linked to a gene for expression in lettuce or the constitutive promoter is operably linked to a nucleotide sequence encoding a signal sequence which is operably linked to a gene for expression in lettuce.

Many different constitutive promoters can be utilized in the instant invention. Exemplary constitutive promoters include, but are not limited to, the promoters from plant viruses such as the 35S promoter from CaMV (Odell, et al., *Nature*, 313:810-812 (1985)) and the promoters from such genes as rice actin (McElroy, et al., *Plant Cell*, 2:163-171 (1990)); ubiquitin (Christensen, et al., *Plant Mol. Biol.*, 12:619-632 (1989) and Christensen, et al., *Plant Mol. Biol.*, 18:675-689 (1992)); pEMU (Last, et al., *Theor. Appl. Genet.*, 81:581-588 (1991)); MAS (Velten, et al., *EMBO J.*, 3:2723-2730 (1984)) and maize H3 histone (Lepetit, et al., *Mol. Gen. Genet.*, 231:276-285 (1992) and Atanassova, et al., *Plant J.*, 2 (3):291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT Application No. WO 96/30530.

C. Tissue-Specific or Tissue-Preferred Promoters:

A tissue-specific promoter is operably linked to a gene for expression in lettuce. Optionally, the tissue-specific promoter is operably linked to a nucleotide sequence encoding a signal sequence which is operably linked to a gene for expression in lettuce. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., *Science*, 23:476-482 (1983) and Sengupta-Gopalan, et al., *PNAS*, 82:3320-3324 (1985)); a leaf-specific and light-induced promoter such as that from cab or rubisco (Simpson, et al., *EMBO J.*, 4(11):2723-2729 (1985) and Timko, et al., *Nature*, 318:579-582 (1985)); an anther-specific promoter such as that from LAT52 (Twell, et al., *Mol. Gen. Genet.*, 217:240-245 (1989)); a pollen-specific promoter such as that from Zm13 (Guerrero, et al., *Mol. Gen. Genet.*, 244:161-168 (1993)) or a microspore-preferred promoter such as that from apg (Twell, et al., *Sex. Plant Reprod.*, 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., *Plant Mol. Biol.*, 20:49 (1992); Close, P. S., Master's Thesis, Iowa State University (1993); Knox, C., et al., "Structure and Organization of Two Divergent Alpha-Amylase Genes from Barley," *Plant Mol. Biol.*, 9:3-17 (1987); Lerner, et al., *Plant Physiol.*, 91:124-129 (1989); Fontes, et al., *Plant Cell*, 3:483-496 (1991); Matsuoka, et al., *PNAS*, 88:834 (1991); Gould, et al., *J. Cell. Biol.*, 108:1657 (1989); Creissen, et al., *Plant J.*, 2:129 (1991); Kalderon, et al., A short amino acid sequence able to specify nuclear location, *Cell*, 39:499-509 (1984); and Steifel, et al., Expression of a maize cell wall hydroxyproline-rich glycoprotein gene in early leaf and root vascular differentiation, *Plant Cell*, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.*, 114:92-6 (1981).

According to a preferred embodiment, the transgenic plant provided for commercial production of foreign protein is lettuce. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see *Methods in Plant Molecular Biology and Biotechnology*, Glick and Thompson Eds., 269: 284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes that Confer Resistance to Pests or Disease and that Encode:

1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., *Science*, 266:789 (1994) (cloning of the tomato Cf-9 gene for resistance to *Cladosporium falvum*); Martin, et al., *Science*, 262:1432 (1993) (tomato Pto gene for resistance to *Pseudomonas syringae* pv. tomato encodes a protein kinase); and Mindrinos, et al., *Cell*, 78:1089 (1994) (Arabidopsis RSP2 gene for resistance to *Pseudomonas syringae*).

2. A *Bacillus thuringiensis* protein, a derivative thereof, or a synthetic polypeptide modeled thereon. See, for example, Geiser, et al., *Gene*, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

3. A lectin. See, for example, the disclosure by Van Damme, et al., *Plant Mol. Biol.*, 24:25 (1994), who disclose the nucleotide sequences of several *Clivia miniata* mannose-binding lectin genes.

4. A vitamin-binding protein such as avidin. See PCT Application No. US 93/06487, the contents of which are hereby incorporated by reference. The application teaches the use of avidin and avidin homologues as larvicides against insect pests.

5. An enzyme inhibitor, for example, a protease or proteinase inhibitor, or an amylase inhibitor. See, for example, Abe, et al., *J. Biol. Chem.*, 262:16793 (1987) (nucleotide sequence of rice cysteine proteinase inhibitor); Huub, et al., *Plant Mol. Biol.*, 21:985 (1993) (nucleotide sequence of cDNA encoding tobacco proteinase inhibitor I); and Sumitani, et al., *Biosci. Biotech. Biochem.*, 57:1243 (1993) (nucleotide sequence of *Streptomyces nitrosporeus* α-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor) and Pratt, et al., *Biochem. Biophys. Res. Comm.*, 163:1243 (1989) (an allostatin is identified in *Diploptera puntata*). See also, U.S. Pat. No. 5,266,317 to Tomalski, et al., who disclose genes encoding insect-specific, paralytic neurotoxins.

8. An insect-specific venom produced in nature, by a snake, a wasp, etc. For example, see Pang, et al., *Gene*, 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Mol. Biol.*, 23:691 (1993), who teach the nucleotide sequence of a cDNA encoding tobacco hornworm chitinase, and Kawalleck, et al., *Plant Mol. Biol.*, 21:673 (1993), who provide the nucleotide sequence of the parsley ubi4-2 polyubiquitin gene.

11. A molecule that stimulates signal transduction. For example, see the disclosure by Botella, et al., *Plant Mol. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., *Plant Sci.*, 89:43 (1993), of heterologous expression of a cecropin-β, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., *Ann. Rev. Phytopathol.*, 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., *Nature*, 366:469 (1993), who show that transgenic plants expressing recombinant antibody genes are protected from virus attack.

17. A developmental-arrestive protein produced in nature by a pathogen or a parasite. Thus, fungal endo-α-1,4-D-polygalacturonases facilitate fungal colonization and plant nutrient released by solubilizing plant cell wall homo-α-1,4-D-galacturonase. See Lamb, et al., *Bio/technology*, 10:1436 (1992). The cloning and characterization of a gene which encodes a bean endopolygalacturonase-inhibiting protein is described by Toubart, et al., *Plant J.*, 2:367 (1992).

18. A developmental-arrestive protein produced in nature by a plant. For example, Logemann, et al., *Bio/technology*, 10:305 (1992), have shown that transgenic plants expressing the barley ribosome-inactivating gene have an increased resistance to fungal disease.

19. A lettuce mosaic potyvirus (LMV) coat protein gene introduced into *Lactuca sativa* in order to increase its resistance to LMV infection. See Dinant, et al., *Mol. Breeding*, 3:1, 75-86 (1997).

Any of the above listed disease or pest resistance genes (1-19) can be introduced into the claimed lettuce variety through a variety of means including but not limited to transformation and crossing.

B. Genes that Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Miki, et al., *Theor. Appl. Genet.*, 80:449 (1990), respectively.

2. Glyphosate (resistance conferred by mutant 5-enolpyruvlshikimate-3-phosphate synthase (EPSPS) and aroA genes, respectively) and other phosphono compounds, such as glufosinate (phosphinothricin acetyl transferase (PAT), dicamba and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. See also, Umaballava-Mobapathie in *Transgenic Research*, 8:1, 33-44 (1999) that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides, such as L-phosphinothricin. The nucleotide sequence of a phosphinothricin-acetyl-transferase gene is provided in European Application No. 0 242 246 to Leemans, et al. DeGreef, et al., *Bio/technology*, 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc1-S3 genes described by Marshall, et al., *Theor. Appl. Genet.*, 83:435 (1992).

3. An herbicide that inhibits photosynthesis, such as a triazine (psbA and gs+ genes) and a benzonitrile (nitrilase gene). Przibilla, et al., *Plant Cell*, 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.*, 285:173 (1992).

4. Acetohydroxy acid synthase, which has been found to make plants that express this enzyme resistant to multiple types of herbicides, has been introduced into a variety of plants. See Hattori, et al., *Mol. Gen. Genet.*, 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.*, 106:17 (1994)), genes for glutathione reductase and superoxide dismutase (Aono, et al., *Plant Cell Physiol.*, 36:1687 (1995)), and genes for various phosphotransferases (Datta, et al., *Plant Mol. Biol.*, 20:619 (1992)).

5. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes (1-5) can be introduced into the claimed lettuce variety through a variety of means including, but not limited to, transformation and crossing.

C. Genes that Confer or Contribute to a Value-Added Trait, Such as:

1. Increased iron content of the lettuce, for example, by introducing into a plant a soybean ferritin gene as described in Goto, et al., *Acta Horticulturae.*, 521, 101-109 (2000).

2. Decreased nitrate content of leaves, for example, by introducing into a lettuce a gene coding for a nitrate reductase. See, for example, Curtis, et al., *Plant Cell Rep.*, 18:11, 889-896 (1999).

3. Increased sweetness of the lettuce by introducing a gene coding for monellin that elicits a flavor 100,000 times sweeter than sugar on a molar basis. See Penarrubia, et al., *Bio/technology*, 10:561-564 (1992).

4. Modified fatty acid metabolism, for example, by introducing into a plant an antisense gene of stearyl-ACP desaturase to increase stearic acid content of the plant. See Knultzon, et al., *PNAS*, 89:2625 (1992).

5. Modified carbohydrate composition effected, for example, by introducing into plants a gene coding for an enzyme that alters the branching pattern of starch. See Shiroza, et al., *J. Bacteriol.*, 170:810 (1988) (nucleotide sequence of *Streptococcus mutants* fructosyltransferase gene); Steinmetz, et al., *Mol. Gen. Genet.*, 20:220 (1985) (nucleotide sequence of *Bacillus subtilis* levansucrase gene); Pen, et al., *Bio/technology*, 10:292 (1992) (production of transgenic plants that express *Bacillus licheniformis* α-amylase); Elliot, et al., *Plant Mol. Biol.*, 21:515 (1993) (nucleotide sequences of tomato invertase genes); Søgaard, et al., *J. Biol. Chem.*, 268:22480 (1993) (site-directed mutagenesis of barley α-amylase gene); and Fisher, et al., *Plant Physiol.*, 102:1045 (1993) (maize endosperm starch branching enzyme II).

D. Genes that Control Male-Sterility:

1. Introduction of a deacetylase gene under the control of a tapetum-specific promoter and with the application of the chemical N-Ac-PPT. See International Publication WO 01/29237.

2. Introduction of various stamen-specific promoters. See International Publications WO 92/13956 and WO 92/13957.

3. Introduction of the barnase and the barstar genes. See Paul, et al., *Plant Mol. Biol.*, 19:611-622 (1992).

Methods for Lettuce Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium*. See, for example, Horsch, et al., *Science,* 227: 1229 (1985); Curtis, et al., *Journal of Experimental Botany,* 45:279, 1441-1449 (1994); Torres, et al., *Plant Cell Tissue and Organ Culture,* 34:3, 279-285 (1993); and Dinant, et al., *Molecular Breeding,* 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.,* 8:238 (1989). See also, U.S. Pat. No. 5,591, 616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation where DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Russell, D. R., et al., *Plant Cell Rep.,* 12 (3, January), 165-169 (1993); Aragao, F. J. L., et al., *Plant Mol. Biol.,* 20 (2, October), 357-359 (1992); Aragao, F. J. L., et al., *Plant Cell Rep.,* 12 (9, July), 483-490 (1993); Aragao, *Theor. Appl. Genet.,* 93:142-150 (1996); Kim, J., Minamikawa, T., *Plant Sci.,* 117:131-138 (1996); Sanford, et al., *Part. Sci. Technol.,* 5:27 (1987); Sanford, J. C., *Trends Biotech.,* 6:299 (1988); Klein, et al., *Bio/technology,* 6:559-563 (1988); Sanford, J. C., *Physiol. Plant,* 7:206 (1990); Klein, et al., *Bio/technology,* 10:268 (1992).

Another method for physical delivery of DNA to plants is sonication of target cells. Zhang, et al., *Bio/technology,* 9:996 (1991). Alternatively, liposome and spheroplast fusion have been used to introduce expression vectors into plants. Deshayes, et al., *EMBO J.,* 4:2731 (1985) and Christou, et al., *PNAS,* 84:3962 (1987). Direct uptake of DNA into protoplasts using $CaCl_2$ precipitation, polyvinyl alcohol, or poly-L-ornithine has also been reported. Hain, et al., *Mol. Gen. Genet.,* 199:161 (1985) and Draper, et al., *Plant Cell Physiol.,* 23:451 (1982). Electroporation of protoplasts and whole cells and tissues have also been described. Saker, M., Kuhne, T., *Biologia Plantarum,* 40(4):507-514 (1997/98); Donn, et al., In Abstracts of VIIth International Congress on Plant Cell and Tissue Culture IAPTC, A2-38, p. 53 (1990); D'Halluin, et al., *Plant Cell,* 4:1495-1505 (1992); and Spencer, et al., *Plant Mol. Biol.,* 24:51-61 (1994). See also Chupean, et al., *Bio/technology,* 7:5, 503-508 (1989).

Following transformation of lettuce target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic lettuce line. Alternatively, a genetic trait which has been engineered into a particular lettuce variety using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "lettuce plant" is used in the context of the present invention, this also includes any gene conversions of that variety. The term "gene converted plant" as used herein refers to those lettuce plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental lettuce plant which contributes the gene for the desired characteristic is termed the "nonrecurrent" or "donor parent." This terminology refers to the fact that the nonrecurrent parent is used one time in the backcross protocol and therefore does not recur. The parental lettuce plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a lettuce plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of lettuce and regeneration of plants therefrom is well known and widely published. For example, reference may be had to Teng, et al., *HortScience,* 27:9, 1030-1032 (1992); Teng, et al., *HortScience,* 28:6, 669-1671 (1993); Zhang, et al., *Journal of Genetics and Breeding,* 46:3, 287-290 (1992); Webb, et al., *Plant Cell Tissue and Organ Culture,* 38:1, 77-79 (1994); Curtis, et al., *Journal of Experimental Botany,* 45:279, 1441-1449 (1994); Nagata, et al., *Journal for the American Society for Horticultural Science,* 125:6, 669-672 (2000); and Ibrahim, et al., *Plant Cell Tissue and Organ Culture,* 28(2), 139-145 (1992). It is clear from the literature that the state of the art is such that these methods of obtaining plants are routinely used and have a very high rate of success. Thus, another aspect of this invention is to provide cells which upon growth and differentiation produce lettuce plants having the physiological and morphological characteristics of variety 'Tamarindo'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The invention is also directed to methods for producing a lettuce plant by crossing a first parent lettuce plant with a second parent lettuce plant where the first or second parent lettuce plant is a lettuce plant of variety 'Tamarindo'. Further, both first and second parent lettuce plants can come from lettuce variety 'Tamarindo'. Thus, any such methods using lettuce variety 'Tamarindo' are part of the invention: selfing, backcrosses, hybrid production, crosses to populations, and the like. All plants produced using lettuce variety 'Tamarindo' as at least one parent are within the scope of this invention, including those developed from varieties derived from lettuce variety 'Tamarindo'. Advantageously, this lettuce variety could be used in crosses with other, different, lettuce plants to produce the first generation ($F_1$) lettuce hybrid seeds and plants with superior characteristics. The variety of the invention can also be used for transformation where exogenous genes are introduced and expressed by the variety of the invention. Genetic variants created either through traditional breeding methods using lettuce variety 'Tamarindo' or through transformation of variety 'Tamarindo' by any of a number of protocols known to those of skill in the art are intended to be within the scope of this invention.

The following describes breeding methods that may be used with lettuce variety 'Tamarindo' in the development of further lettuce plants. One such embodiment is a method for developing variety 'Tamarindo' progeny lettuce plants in a lettuce plant breeding program, by: obtaining the lettuce plant, or a part thereof, of variety 'Tamarindo', utilizing said plant or plant part as a source of breeding material, and selecting a lettuce variety 'Tamarindo' progeny plant with molecular markers in common with variety 'Tamarindo' and/or with morphological and/or physiological characteristics selected from the characteristics listed in the section entitled "Objective description of the variety 'Tamarindo'." Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety 'Tamarindo' progeny lettuce plants, by crossing variety 'Tamarindo' with another lettuce plant, thereby producing a population of lettuce plants, which, on average, derive 50% of their alleles from lettuce variety 'Tamarindo'. A plant of this population may be selected and repeatedly selfed or sibbed with a lettuce variety resulting from these successive filial generations. One embodiment of this invention is the lettuce variety produced by this method and that has obtained at least 50% of its alleles from lettuce variety 'Tamarindo'. One of ordinary skill in the art of plant breeding would know how to evaluate the traits of two plant varieties to determine if there is no significant difference between the two traits expressed by those varieties. For example, see Fehr and Walt, *Principles of Variety Development,* pp. 261-286 (1987). Thus the invention includes lettuce variety 'Tamarindo' progeny lettuce plants containing a combination of at least two variety 'Tamarindo' traits selected from those listed in the section entitled "Objective description of the variety 'Tamarindo'," or the variety 'Tamarindo' combination of traits listed in the Summary of the Invention, so that said progeny lettuce plant is not significantly different for said traits than lettuce variety 'Tamarindo' as determined at the 5% significance level when grown in the same environmental conditions. Using techniques described herein, molecular markers may be used to identify said progeny plant as a lettuce variety 'Tamarindo' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of lettuce variety 'Tamarindo' may also be characterized through their filial relationship with lettuce variety 'Tamarindo', as for example, being within a certain number of breeding crosses of lettuce variety 'Tamarindo'. A breeding cross is a cross made to introduce new genetics into the progeny, and is distinguished from a cross, such as a self or a sib cross, made to select among existing genetic alleles. The lower the number of breeding crosses in the pedigree, the closer the relationship between lettuce variety 'Tamarindo' and its progeny. For example, progeny produced by the methods described herein may be within 1, 2, 3, 4, or 5 breeding crosses of lettuce variety 'Tamarindo'.

As used herein, the term "plant" includes plant cells, plant protoplasts, plant cell tissue cultures from which lettuce plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the lettuce variety 'Tamarindo' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same variety with the American Type Culture Collection, (ATCC), P.O. Box 1549, MANASSAS, VA 20108 USA.

At least 2500 seeds of lettuce variety 'Tamarindo' were deposited on Oct. 5, 2012 according to the Budapest Treaty in the American Type Culture Collection (ATCC), ATCC Patent Depository, 10801 University Boulevard, Manassas, Va., 20110, USA. The deposit has been assigned ATCC number PTA-13146. Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed.

The deposit will be maintained in the ATCC depository, which is a public depository, for a period of 30 years, or 5 years after the most recent request, or for the effective life of the patent, whichever is longer, and will be replaced if a deposit becomes nonviable during that period.

The invention claimed is:

1. Lettuce seed designated as 'Tamarindo', representative sample of seed having been deposited under ATCC Accession Number PTA-13146.

2. A lettuce plant produced by growing the seed of claim 1.

3. A plant part from the plant of claim 2.

4. The plant part of claim 3 wherein said part is a head, a leaf, or a portion thereof.

5. A lettuce plant having all the physiological and morphological characteristics of the lettuce plant of claim 2.

6. A plant part from the plant of claim 5.

7. The plant part of claim 6, wherein said part is a head, a leaf, or a portion thereof.

8. An $F_1$ hybrid lettuce plant having 'Tamarindo' as a parent where 'Tamarindo' is grown from the seed of claim 1.

9. Pollen or an ovule of the plant of claim 2.

10. A tissue culture of the plant of claim 2.

11. A lettuce plant regenerated from the tissue culture of claim 10, wherein the plant has all of the morphological and physiological characteristics of a lettuce plant produced by growing seed designated as 'Tamarindo' having ATCC Accession Number PTA-13146.

12. A method of making lettuce seeds, said method comprising crossing the plant of claim 2 with another lettuce plant and harvesting seed therefrom.

13. A method of making lettuce variety 'Tamarindo', said method comprising selecting seeds from the cross of one 'Tamarindo' plant with another 'Tamarindo' plant, a sample of 'Tamarindo' lettuce seed having been deposited under ATCC Accession No. PTA-13146.

* * * * *